(12) United States Patent
Fleuren

(10) Patent No.: US 9,877,540 B2
(45) Date of Patent: Jan. 30, 2018

(54) ASSEMBLY COMPRISING A SHOE, A SHAPED PIECE CONNECTED WITH THE SHOE TO SUPPORT THE ANKLE, AND A SET OF A SHAPED PIECE AND FIXING MEANS FOR ATTACHMENT TO THE SHOE

(75) Inventor: Marcel Johan Dalitso Fleuren, Delft (NL)

(73) Assignee: Exo Ligament B.V., Delft (NL)

( * ) Notice: Subject to any disclaimer, the term of this patent is extended or adjusted under 35 U.S.C. 154(b) by 247 days.

(21) Appl. No.: 14/125,419

(22) PCT Filed: Jun. 11, 2012

(86) PCT No.: PCT/NL2012/050405
§ 371 (c)(1),
(2), (4) Date: Feb. 6, 2014

(87) PCT Pub. No.: WO2012/169895
PCT Pub. Date: Dec. 13, 2012

(65) Prior Publication Data
US 2014/0223775 A1 Aug. 14, 2014

(30) Foreign Application Priority Data

Jun. 10, 2011 (NL) ...................................... 2006925
Apr. 2, 2012 (NL) ...................................... 2008587

(51) Int. Cl.
*A43B 7/20* (2006.01)
*A43B 7/14* (2006.01)
(Continued)

(52) U.S. Cl.
CPC .................. *A43B 7/14* (2013.01); *A43B 7/18* (2013.01); *A43B 7/20* (2013.01); *A61F 5/01* (2013.01);
(Continued)

(58) Field of Classification Search
CPC .... A43B 7/14; A43B 7/20; A43B 7/18; A61F 5/01; A61F 5/0111; A61F 5/0195; A61F 2005/0181
(Continued)

(56) References Cited

U.S. PATENT DOCUMENTS 1,155,506 A * 10/1915 Osaki ....................... A43B 7/20
  36/136
2,617,207 A * 11/1952 Jennett ................ A43B 5/1691
  2/22
(Continued)

FOREIGN PATENT DOCUMENTS

WO  8910111 A1  11/1989

OTHER PUBLICATIONS

International Search Report, dated Jan. 17, 2013, from corresponding PCT application.

*Primary Examiner* — Marie Bays
(74) *Attorney, Agent, or Firm* — NLO N.V.; Catherine A. Shultz

(57) ABSTRACT

An assembly includes a shoe and a device connected with the shoe to support the ankle, wherein the device includes a shaped piece which surrounds the ankle at least at the rear and is formed corresponding to the malleoli of the ankle. A shaped piece and a shoe suitable for use in the assembly and a set of the shaped piece and a fixing element for attachment to a shoe are also described.

20 Claims, 4 Drawing Sheets

(51) Int. Cl.
*A61F 5/01* (2006.01)
*A43B 7/18* (2006.01)
*A63B 71/12* (2006.01)

(52) U.S. Cl.
CPC .......... *A61F 5/0111* (2013.01); *A61F 5/0127* (2013.01); *A63B 2071/1275* (2013.01)

(58) Field of Classification Search
USPC .............................. 36/88, 89, 92; 602/27, 28
See application file for complete search history.

(56) References Cited

U.S. PATENT DOCUMENTS

| | | | | |
|---|---|---|---|---|
| 4,523,394 A * | 6/1985 | Lindh | ................... | A61F 5/0111 36/114 |
| 4,547,981 A * | 10/1985 | Thais | ................... | A43B 7/00 36/114 |
| 4,556,054 A * | 12/1985 | Paulseth | ............... | A61F 5/0111 602/27 |
| 4,670,998 A * | 6/1987 | Pasternak | ................ | A43B 5/00 36/114 |
| 4,817,589 A * | 4/1989 | Wertz | ................... | A61F 5/0111 602/28 |
| 4,865,023 A * | 9/1989 | Craythorne | ........... | A61F 5/0111 602/27 |
| 4,922,630 A * | 5/1990 | Robinson | ................ | A43B 5/00 36/89 |
| 4,982,733 A * | 1/1991 | Broadhurst | ........... | A61F 5/0111 602/27 |
| 5,175,947 A * | 1/1993 | Parracho | ................. | A43B 5/00 36/132 |
| 5,438,769 A * | 8/1995 | Mazzarolo | ............... | A43B 3/02 36/131 |
| 5,449,005 A * | 9/1995 | Echols | ................... | A61F 5/0111 128/882 |
| 5,775,006 A * | 7/1998 | Breuner | ................... | A43B 3/02 36/45 |
| 5,778,563 A | 7/1998 | Ahlbaumer | | |
| 5,921,947 A | 7/1999 | Kessler | | |
| 5,924,706 A * | 7/1999 | Seltzer | ................. | A43B 5/1625 280/11.3 |
| 5,946,827 A * | 9/1999 | Okajima | ............... | A43B 5/0401 36/117.6 |
| 5,966,843 A * | 10/1999 | Sand | ........................ | A43B 7/20 36/115 |
| 6,032,286 A * | 3/2000 | Thomas | ................ | A61F 5/0111 128/892 |
| 6,053,884 A * | 4/2000 | Peters | ................... | A61F 5/0127 602/16 |
| 6,073,370 A * | 6/2000 | Okajima | ............... | A43B 5/04 36/50.1 |
| 6,079,128 A * | 6/2000 | Hoshizaki | ............... | A43B 23/16 36/115 |
| 6,168,172 B1 * | 1/2001 | Meibock | ............... | A43B 5/0401 280/11.221 |
| 6,503,218 B1 * | 1/2003 | Ascheman | ............... | A61F 5/0111 602/23 |
| 6,692,454 B1 * | 2/2004 | Townsend | ................ | A43B 5/10 128/882 |
| 6,725,577 B2 * | 4/2004 | Mazzarolo | ............... | A43B 3/02 36/131 |
| 6,858,017 B2 * | 2/2005 | Peters | ................... | A61F 5/0127 602/16 |
| 6,883,256 B2 * | 4/2005 | Mazzarolo | ............... | A43B 3/02 36/131 |
| 7,022,096 B1 * | 4/2006 | Alfieri | ................ | A63B 71/1225 602/23 |
| 7,171,766 B2 * | 2/2007 | Bouche | ................... | A43B 7/20 36/89 |
| 7,219,444 B2 * | 5/2007 | Hall | ...................... | A43B 5/0401 36/10 |
| 7,398,607 B1 * | 7/2008 | Garcia | ................ | A43B 1/0072 36/101 |
| 7,458,950 B1 * | 12/2008 | Ivany | ...................... | A43B 7/14 36/136 |
| 7,666,158 B2 * | 2/2010 | Jacobsen | ............... | A61F 5/0113 36/136 |
| 8,245,419 B2 * | 8/2012 | Echols | .................... | A43B 7/20 36/114 |
| 8,657,773 B2 * | 2/2014 | Ostergard | ............. | A61F 5/0111 36/88 |
| 2003/0115775 A1 * | 6/2003 | Mazzarolo | ............... | A43B 3/02 36/89 |
| 2004/0194350 A1 * | 10/2004 | Mazzarolo | ............... | A43B 3/02 36/131 |
| 2005/0126044 A1 * | 6/2005 | Langley | .................... | A43B 7/20 36/89 |
| 2005/0177083 A1 * | 8/2005 | Heil | ...................... | A61F 5/0111 602/27 |
| 2005/0193594 A1 * | 9/2005 | Murphy | ................ | A43B 5/1616 36/89 |
| 2006/0075661 A1 * | 4/2006 | Ramsey | ................ | A43B 3/0078 36/89 |
| 2006/0179686 A1 * | 8/2006 | Labonte | ............... | A43B 5/1691 36/89 |
| 2007/0056189 A1 * | 3/2007 | Schafer Mathison | ............ | A43B 1/0018 36/89 |
| 2007/0060852 A1 * | 3/2007 | Heil | ...................... | A61F 5/0111 602/23 |
| 2008/0082034 A1 | 4/2008 | Wilkerson | | |
| 2010/0076361 A1 * | 3/2010 | Kruijsen | ............... | A61F 5/0113 602/28 |
| 2010/0319217 A1 * | 12/2010 | Echols | ............... | A43B 23/0285 36/89 |
| 2013/0012855 A1 * | 1/2013 | Giza | ..................... | A61F 5/0111 602/27 |
| 2013/0237894 A1 * | 9/2013 | Lundberg | ............... | A61F 5/0111 602/27 |
| 2014/0223775 A1 * | 8/2014 | Fleuren | ................ | A61F 5/0111 36/89 |
| 2014/0276318 A1 * | 9/2014 | Faux | ..................... | A61F 5/0109 602/28 |
| 2016/0067075 A1 * | 3/2016 | Malinowski | .......... | A61F 5/0113 602/28 |

* cited by examiner

ASSEMBLY COMPRISING A SHOE, A SHAPED PIECE CONNECTED WITH THE SHOE TO SUPPORT THE ANKLE, AND A SET OF A SHAPED PIECE AND FIXING MEANS FOR ATTACHMENT TO THE SHOE

BACKGROUND OF THE INVENTION

Field of the Invention

The invention relates to an assembly comprising a shoe and a device connected with the shoe to support the ankle.

Description of the Related Art

Such an assembly is known from U.S. Pat. No. 5,792,087. The assembly described here is fitted with a shoe and an ankle support which is attached to the user's lower leg by means of a strap. From this strap a pair of support elements extends on either side of the ankle. The support elements are attached to the shoe with a bracket around the heel and sole of the shoe. Because the support elements are on both sides of the ankle, bending of the ankle towards the inside and outside is limited while dorsal flexion (movement of the foot towards the shin) and plantar flexion (movement of the foot away from the shin) remain possible.

One disadvantage of the assembly from the prior art is that the support elements are relatively cumbersome, whereby the freedom of movement of the foot is restricted unnecessarily and user comfort of this assembly is relatively low.

Another disadvantage is that the assembly from the prior art is relatively ineffective for countering dislocations other than those resulting from supination.

BRIEF SUMMARY OF THE INVENTION

One object of the invention is to provide an assembly which does not unnecessarily reduce the freedome of movement of the foot and gives a relatively higher user comfort.

A further objective of the invention is to provide an assembly which effectively counters damage to the ankle ligaments, namely the lateral ankle ligaments, in particular as a result of inversion.

For this purpose the assembly according to the invention is characterized in that the device comprises a shaped piece which surrounds the ankle at least at the back and which is formed corresponding to the ankle malleoli.

Because the shaped piece is formed to the malleoli of the ankle, on dislocation a more effective transfer of forces is achieved from the shoe to the leg of the user, in particular the malleoli, whereby damage resulting from dislocation is countered more effectively, particularly that resulting from inversion, and in addition for example eversion. Because the shaped piece is formed to the malleoli and at least partly surrounds the ankle at the back, the shaped piece takes up relatively less space in the area around the ankle, whereby the freedom of movement is not reduced unnecessarily and user comfort is increased. Also by forming the shaped piece to the anatomy of the malleoli of the user's ankle, an increase in user comfort is achieved, as the forces occurring during dislocation are distributed over a relatively larger area.

In one embodiment the shaped piece has an outer shaped region which is formed corresponding to the lateral malleolus. This outer shaped region can extend fully or partly over the lateral malleolus.

In a further embodiment the shaped piece has an inner shaped region which is formed corresponding to the medial malleolus. This inner shaped region, like the outer shaped region, can extend fully or partly over the medial malleolus. Both the inner and the outer shaped regions can advantageously be fitted with padding to transfer the forces occurring on dislocation to the malleoli in a more comfortable manner.

Another embodiment concerns an assembly wherein the shaped piece has a rear shaped region which is at a distance from the Achilles' tendon. Preferably between the rear moulding region and the Achilles' tendon, a cavity is formed to create movement space for the Achilles' tendon or tendo calcaneus, which tendon runs from the heel bone to the calf muscle. Here the rear shaped region is located at a distance directly behind the Achilles' tendon, forming a cavity between the rear shaped region and the Achilles' tendon. One alternative is the formation of a recess in the rear shaped region at the site of the Achilles' tendon, which recess extends in the rear shaped region from one side of the rear moulding region towards the heel so that the Achilles' tendon can move freely. Here the support part of the lateral malleolus and the support part of the medial malleolus extend freely from the rear shaped region to the shoe. A combination of said embodiments is also possible. Because the rear shaped region is located at a distance from the Achilles' tendon, the Achilles' tendon can move freely, giving the user's foot a greater freedom of movement.

A further embodiment concerns an assembly in which the shaped piece has opposing cheeks which are located on either side of the ankle, which cheeks at the front determine an opening via which the ankle can be received in the shaped piece. The shaped piece is thus relatively easy to apply over the ankle via the opening at the front.

In a further embodiment the shoe is fitted with an upper and a sole, wherein the assembly comprises a connecting means which extends at an angle of less than 90° in relation to the sole from the shaped piece of the device in the direction of the upper. The connecting means functions as an external ligament whereby the ligaments present in the foot are better protected on dislocation.

A further embodiment concerns an assembly wherein the connecting means is attached to at least one of an inner and outer side of the upper. By attaching the connecting means to an inside and outside of the upper, a relatively better protection is obtained against dislocation. Particularly the connection to the outside of the upper is advantageous for countering dislocation as a result of inversion movements.

It can be advantageous to attach the connecting means to an insole of the shoe. It is advantageous here that if the insole with integrated connecting means can be introduced into and removed from the shoe, the shaped piece can be used for several shoes separately.

In a further embodiment the connecting means comprises a first and a second end, wherein the first end is attached to the shaped piece and the second end is attached to the upper. Thus a relative optimum protection is obtained of the outside ligaments against dislocation, wherein the connecting means is also relatively easily accessible, for example for loosening or tightening by the user.

A further embodiment concerns an assembly wherein the connecting means comprises a first and a second connecting part, wherein the first part extends between the shaped piece near the lateral malleolus and a fixing means connected with the shoe, and the second part extends between the fixing means and the shaped piece near the medial malleolus. Thus on dislocation a relatively better transfer of forces is achieved from the upper to the shaped piece, wherein the forces occurring are also distributed better over the moulding and the malleoli. It is for example advantageous for the connecting means or connecting parts to comprise straps or cords. Preferably the fixing means is attached to the shoe at a transition between the instep and a side of the shoe, wherein the fixing means is located between the malleoli and the upper.

In yet a further embodiment the connecting means comprises a further connecting part with a first and a second part, wherein the first part extends between the sole of the shoe near the upper and the fixing means, and the second part extends between the fixing means and the sole of the shoe near the heel. The ends of the first and/or second part can hereby touch the sole or be integrated therein. At the site of the shoe between the first and second part, no extra reinforcement need then be applied because the further connecting part provides extra rigidity. A further advantage is that the part of the metatarsus protruding proximally is thus given extra freedom of movement. Other methods of reinforcement are of course also conceivable, namely those in which space is left at the said proximally protruding part of the metatarsus. The first and second parts can be mounted on one side of the shoe but can also be integrated in the side of the shoe.

It can be advantageous to attach the further connecting part to an insole of the shoe. The advantage here is that if the insole with integral further connecting part can subsequently be introduced into and removed from the shoe, the shaped piece can be used in several shoes separately.

In another embodiment the connecting means comprises a connection element with a first and a second part, wherein the first part extends from the fixing means in the direction of the sole of the shoe near the upper, and the second part extends from the fixing means in the direction of the sole of the shoe near the heel. The first and second part extend from the instep part over part of the outside or inside of the shoe but do not touch the sole.

Preferably the fixing element comprises a patch wherein the first and the second part of the patch comprise fixing means for attachment to the shoe. The patch can be attached to the outside of the shoe by stitching, for which recesses to be created in advance can be provided in the patch, but this can also possibly be achieved with an adhesive on the side of the patch facing the shoe. It is also possible to integrate the patch in the shoe. The patch can also be attached to or integrated in the inside of the shoe depending on the desired reinforcement of the ankle, such as inversion or eversion.

To connect the shaped piece to the fixing means so as to produce the assembly, the fixing means preferably comprises an engaging means for engaging the connecting means. The engaging means then engages the first and second connecting parts so that the shaped piece can be attached to the shoe. The engaging means can be hook-shaped but can also comprise an integral passage or ring. Preferably the engaging means and the fixing means form an integral unit.

The invention also concerns a shaped piece suitable for use in an assembly according to the invention.

In one embodiment the shaped piece is fitted with an outer shaped region which is formed corresponding to the lateral malleolus. This outer shaped region can as stated extend fully or partly over the lateral malleolus.

A further embodiment concerns a shaped piece fitted with an inner shaped region formed corresponding to the medial malleolus.

A further embodiment concerns a shaped piece fitted with a rear shaped region located at a distance from the Achilles' tendon. Because the rear shaped region is located at a distance from the Achilles' tendon, the Achilles' tendon can move freely, giving the user's foot a greater freedom of movement.

Yet a further embodiment concerns a shaped piece fitted with opposing cheeks located on either side of the ankle, which cheeks at the front determine an opening via which the ankle can be received in the shaped piece. In this manner as stated, the moulding is relatively easy to apply over the ankle by means of the opening at the front.

In yet a further embodiment of the shaped piece, reinforcements are attached to the rear shaped region. The reinforcements give the shaped piece a relatively higher degree of form stability.

It is furthermore conceivable that a universal set of shaped pieces of different sizes is produced or that a shaped piece is custom-made. A combination of a shaped piece from a universal set and a custom-made part, such as a shaped piece made of at least two parts, is also a possibility. The shaped piece or the custom-made part can thus advantageously be made for example of plastically deformable materials such as a thermoplastic, or hardening materials such as a thermosetting plastic, wherein the shaped piece or custom-made part is adapted to the anatomy of the user's ankle. Also combinations of the above materials are possible. Also another rigid material such as a composite material can be used.

The shaped piece can furthermore be fitted with engaging means such as a clip or clamp for engaging the first and/or second part of the connecting means. It is also possible to provide accommodation means for ends (of the parts) of the connecting means in the shaped piece so that these ends can be concealed.

The invention furthermore comprises a shoe suitable for use in an assembly according to the invention.

One embodiment concerns a shoe fitted with a fixing means for attaching the connecting means to the upper. It is possible to attach these connecting means to finished shoes by means of stitching or another attachment means. It is also possible to fit a fixing means to the upper in advance, on production of the shoe, so as to prevent reduction in the rigidity of the shoe, for example by cutting or chopping into the shoe.

Yet a further embodiment concerns a shoe wherein the fixing means is attached to an outside i.e. the lateral side of the upper. By attaching the fixing means to the outside of the upper, a relatively optimum force transfer from the shoe to the shaped piece is obtained. The fixing means can also be attached to the inside of the shoe to counter dislocation other than that resulting from an inversion movement. Preferably the fixing means is attached to the shoe at a transition between the instep and a side of the shoe, wherein the fixing means is located between the malleoli and the upper.

Yet a further embodiment concerns a shoe in which the fixing means comprises a fixing ring. A ring is ideal for use for example in combination with a strap. It is also conceivable that other methods of fixing are used, such as fixing by means of hook-and-loop tape, buckles, cord or similar, or other special fixing means developed for the assembly.

The invention furthermore relates to a set of the shaped piece as described above and a fixing element for attachment to a shoe, which fixing element comprises a first and a second part, wherein the first part and the second part extend from each other at an angle of between greater than or equal to 0° and 180°. The moulding and the fixing element as described above can be produced with a shoe as an assembly. However it is also possible to produce the shaped piece as described above and a fixing element for attachment to a shoe. The fixing element is then suitable for fixing to an arbitrary shoe so that the moulding can be used with any desired shoe. It is also possible to produce the fixing element separately for attachment to an arbitrary shoe for use with the shaped piece.

Preferably the first part and the second part enclose a capital lambda (Λ) shape or inverted V shape or boomerang shape, wherein the angle enclosed is between 70° and 120°. Preferably the fixing element comprises a first and a second part which enclose an angle of greater than 90°. This angle makes it possible that the force transfer to the shoe on inversion is relatively optimum by distribution over the upper and the heel of the shoe.

In one embodiment the fixing element comprises a patch wherein the first and second part of the patch comprise fixing means for attachment to the shoe. The patch can for example be prepared for stitching the fixing element onto the shoe. It is however also possible for a layer of adhesive such as a glue to be applied to a side of the patch to be facing the shoe.

Preferably the fixing means comprises an engaging means for engaging the connecting means. This engaging means can be hook-shaped but an integrated ring or passage on the patch is also possible. Preferably the engaging means and the fixing means form an integral whole.

BRIEF DESCRIPTION OF THE DRAWINGS

The invention will be explained below in more detail with reference to embodiments shown in FIGS. 1 to 5 of an assembly according to the invention.

DETAILED DESCRIPTION OF THE PREFERRED EMBODIMENTS

Figure 1:
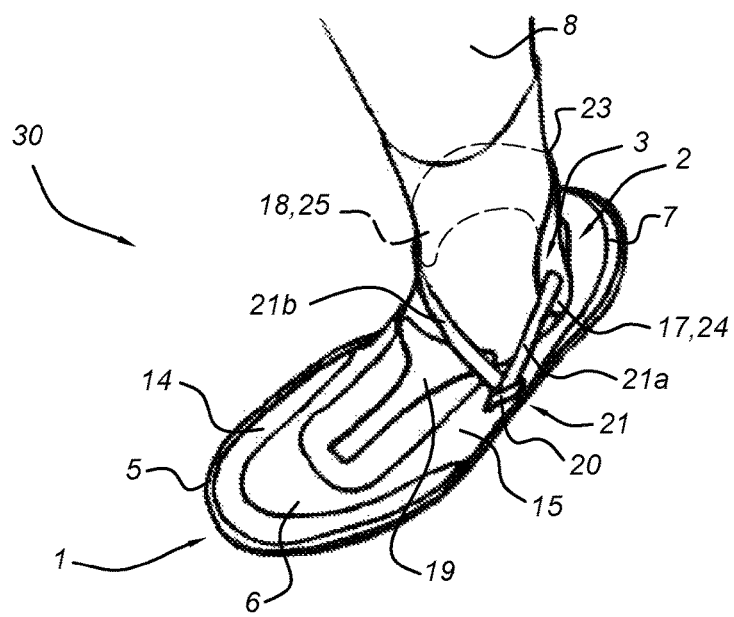
FIG. 1 shows an embodiment of an assembly according to the invention fitted with a shoe with a device according to the invention, wherein the shaped piece has the form of a semi-open rigid clip.

FIG. 1 shows an embodiment of an assembly 30 according to the invention fitted with a shoe 1 with a device 2, wherein the shaped piece 3 has the form of a semi-open, rigid clip. The foot is shown in a state inverted in relation to the lower leg 8, a state which is a combination of plantar flexion, supination and adduction. This state is one of the most common dislocation states.

The open side of the clip 3 is located at the front of the lower leg 8 above the instep part of the shoe 19. The clip 3 rests with support parts 24, 25 on the rear of the lateral malleolus 17 and medial malleolus 18 respectively. It is also possible that the support parts 24, 25 clasp around the malleoli 17, 18. On the back of the clip 3 is a cavity 23 to provide freedom of movement for the Achilles' tendon or tendo calcaneus. Near the instep part of the shoe 19 on the outside 15 of the shoe is mounted a fixing ring 20. Through the fixing ring 20 runs a connecting means 12 in the form of a strap 21 which connects the support parts 24, 25 together and to the shoe. An instep part 21b of the strap 21 then lies between the fixing ring 20 and support part 25, an outer part 21a of the strap 21 lies between the fixing ring 20 and support part 24. The fixing ring 20 can also be produced with the shoe 1 as an integral component, for example an injection moulding.

The inversion movement is countered because the outside 15 of the shoe 1 moves with the fixing ring 20 away from the support parts 24 and 25, exerting a tensile force on the strap 21. The strap 21 acts as a type of external ligament and offers resistance to the tensile force exerted. This prevents injury to the ankle ligaments or other parts of the foot. It is important that the part of the outside 15 of the shoe 1 which lies in the extension of the strap parts 21a, 21b is formed sufficiently rigid. The resistance offered by the strap 21 can be made adjustable, for example by means of a rotation wheel or by pulling the strap 21 with a fastening on the clip 3 or shoe 1 so that the ratio between firstly the freedom of movement and secondly protection against dislocation is controllable.

Because the clip 3 is preferably reinforced at the back of the cavity 23, it is also prevented that on an inversion movement, the clip 3 is drawn over the malleoli 17, 18 by the band 21, whereby the assembly remains stable.

Figure 2A:
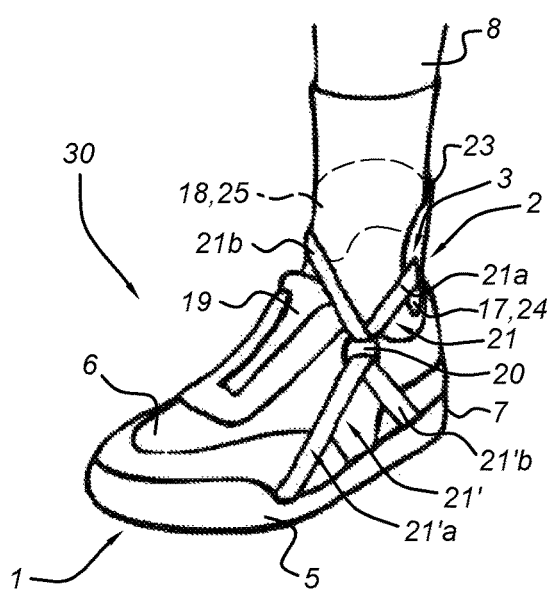
FIG. 2a shows the shoe with the clip in FIG. 1, wherein the foot is standing flat on the ground.

FIG. 2a shows the shoe 1 with the clip 3 from FIG. 2 wherein the foot is standing flat on the ground. It is also shown that on the outside 15 of the shoe 1 is attached a further strap 21' between the fixing ring 20 and the sole 5 below the strap 21. The strap 21' serves as extra reinforcement for the exterior of the shoe 1. The strap 21' has a hook part 21'b which extends between the fixing ring 20 and the sole 5/heel 7, and an upper part 21'a which extends between the fixing ring 20 and the sole 5 of the upper 6. On an extreme inversion movement, the strap 21' provides extra resistance to tensile forces. Because no extra reinforcement is necessary in the shoe 1 at the site of the strap 21', particularly between strap parts 21'a and 21'b, the freedom of movement of the bone parts and/or joints present on the outside of the foot is increased, in particular the proximally protruding part of the metatarsus, whereby the user will experience a higher comfort. It is possible that the strap 21' continues into the sole and is attached hereon. It is furthermore possible that the strap 21' is located fully inside the shoe and is attached to the insole.

Figure 2B:
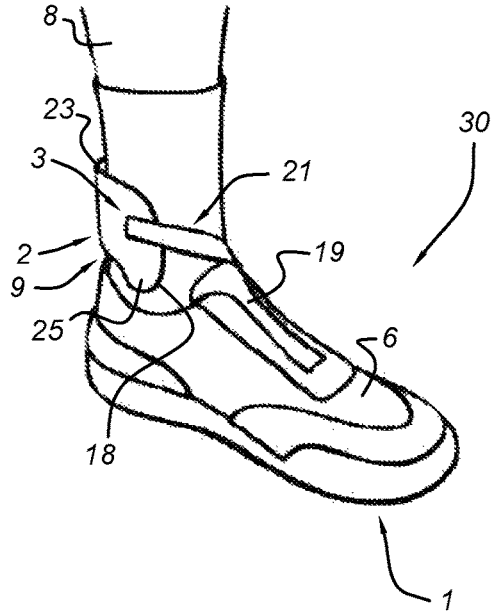
FIG. 2b shows the embodiment of the shoe with clip in FIGS. 1 and 2a, but on the inside of the foot.

FIG. 2b shows the embodiment of the shoe 1 with clip 3 of FIGS. 1 and 2a but on the inside of the foot. FIG. 2b also shows how the strap 21 is connected with the support part 25. It can also be seen that the support part 25 has a rounded form to increase the wearing comfort in the region around the medial malleolus 18, in particular when relatively great forces are exerted. The addition of padding increases the comfort further and improves the distribution of forces.

Figure 3A:
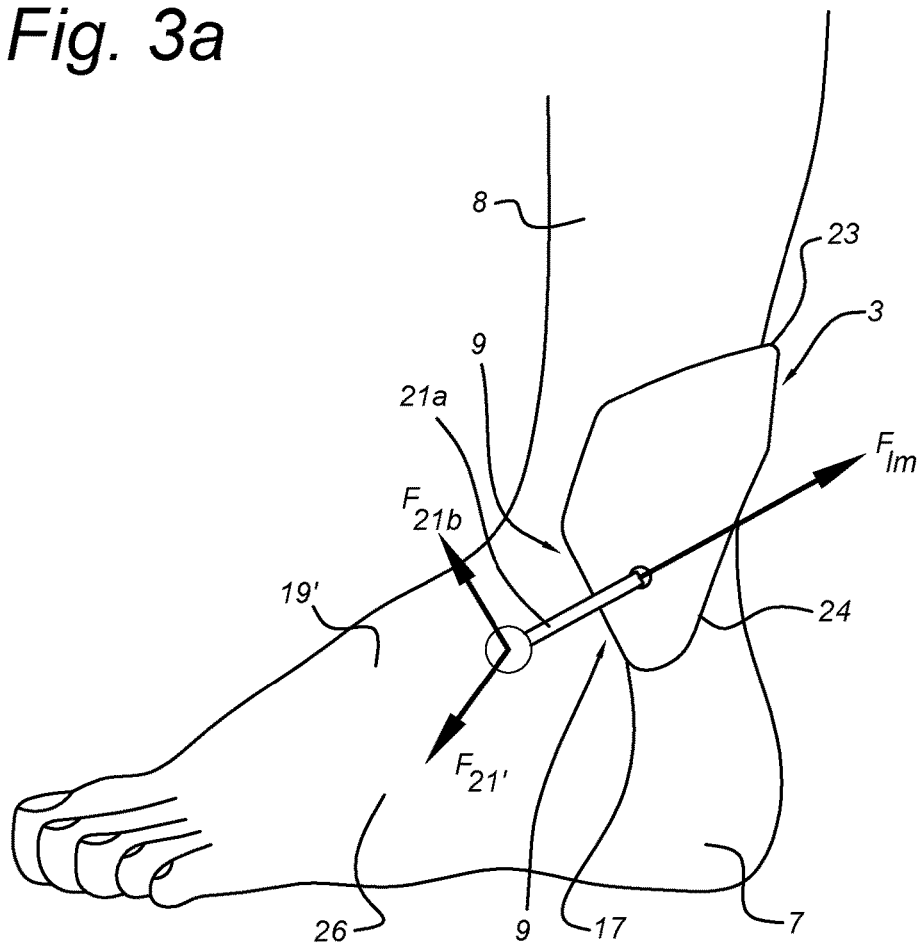
FIG. 3a shows a side view of the outside of a foot with the embodiment of the clip in FIGS. 1, 2a, 2b and 5, wherein the forces occurring on inversion are shown.

FIG. 3a shows a side view from the outside of a foot with the embodiment of the clip 3 of FIGS. 1, 2a and 2b, wherein the forces occurring on inversion are shown. FIG. 3a shows the three force vectors $F_{21b}$, $F_{21'}$ and $F_{lm}$, wherein $F_{21b}$ is the force on the fixing ring 20 which is exerted on inversion by strap part 21b, $F_{21'}$ is the force exerted on the fixing ring 20 by strap 21' or the shoe 1, and $F_{lm}$ is the reaction force exerted by the lateral malleolus 17 on the clip 3.

Figure 3B:
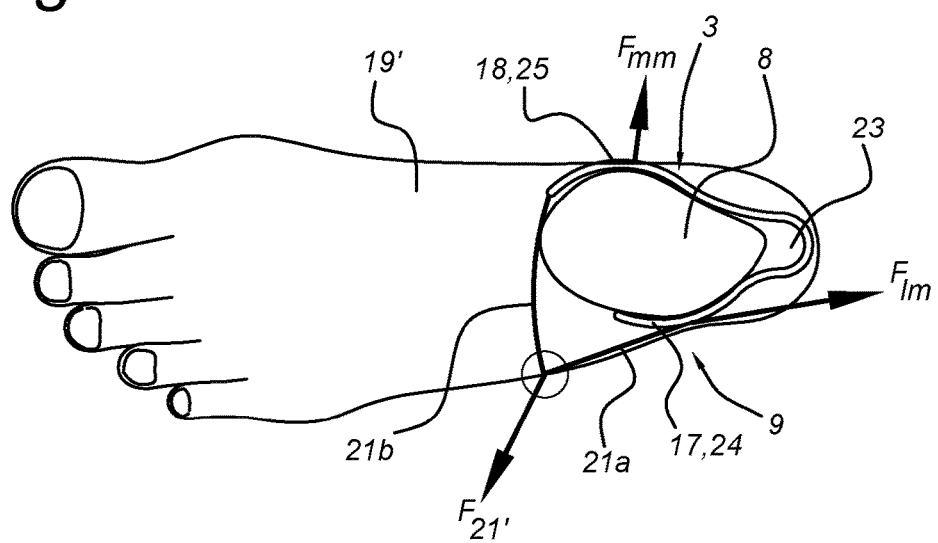
FIG. 3b shows a top view of the foot from FIG. 3a with an embodiment of the clip from FIGS. 1, 2a, 2b and 5, wherein again the forces occurring on inversion are shown.

FIG. 3b shows a top view of the foot in FIG. 3a with an embodiment of the clip 3 of FIGS. 1, 2a and 2b, wherein again the forces occurring on inversion are shown. On inversion, strap 21' exerts a force $F_{21'}$ on the fixing ring 20 which transmits this force via strap parts 21a and 21b to the clip 3. Because the clip 3 rests via support parts 24, 25 on malleoli 17, 18, this force is transferred to these malleoli 17, 18. Thus reaction forces $F_{lm}$ and $F_{mm}$ occur from the malleoli 17, 18.

Furthermore FIG. 3b shows how the clip 3 surrounds the malleoli 17, 18. It is also shown how the cavity 23 leaves room for the Achilles' tendon such that the freedom of movement of this tendon and thus the foot is increased.

Figure 4:
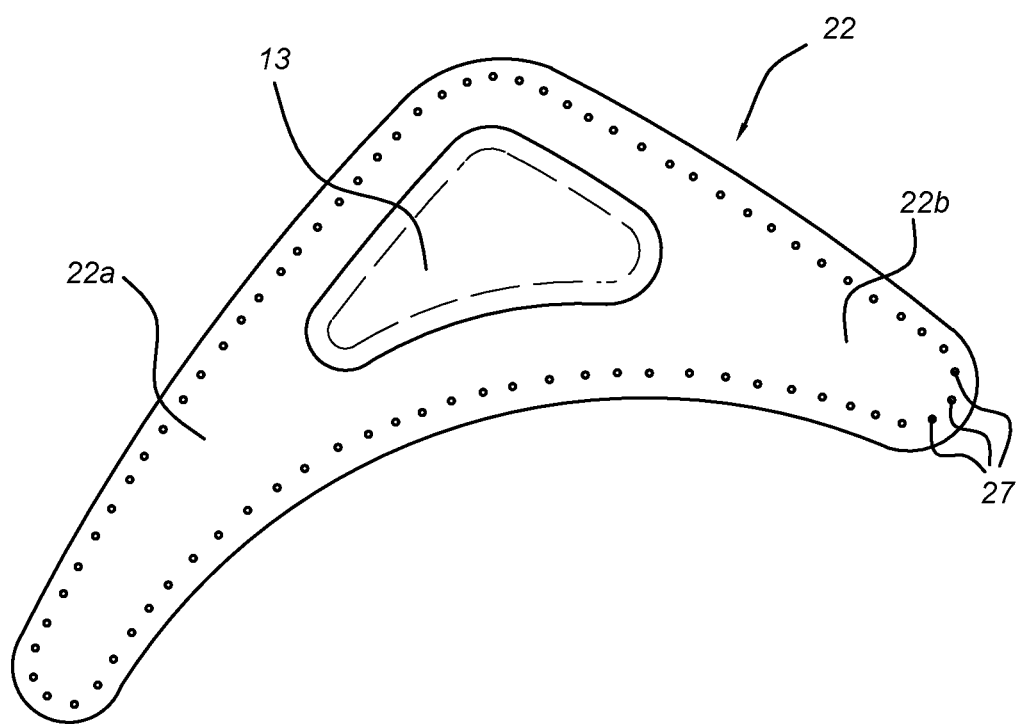
FIG. 4 shows an embodiment of the connecting means for assembling the assembly in FIG. 2a, FIG. 5 shows an embodiment of the assembly of the shoe with the clip in FIG. 2, wherein the foot is standing flat on the ground.

FIG. 4 shows an embodiment of the connecting means 12 for mutual connection of the clip and the shoe, or assembling the assembly from FIG. 2a. The connecting means 12 comprises a patch 22 with first and second parts 22a, 22b. The first part 22a and the second part 22b extend from each other at an angle of between greater than or equal to 0° and 180° so as to form a capital lambda (Λ) shape, a boomerang shape or an inverted V shape, wherein the enclosed angle is preferably between 90° and 120°. The patch 22 furthermore comprises a fixing means 13, in FIGS. 4 and 5 in the form of engaging means for engaging the strap 21 of the clip 3. The engaging means can be designed in the form of a hook. It is also possible that the fixing means is designed as an integral passage or ring for the strap 21 in the patch 22.

Figure 5:
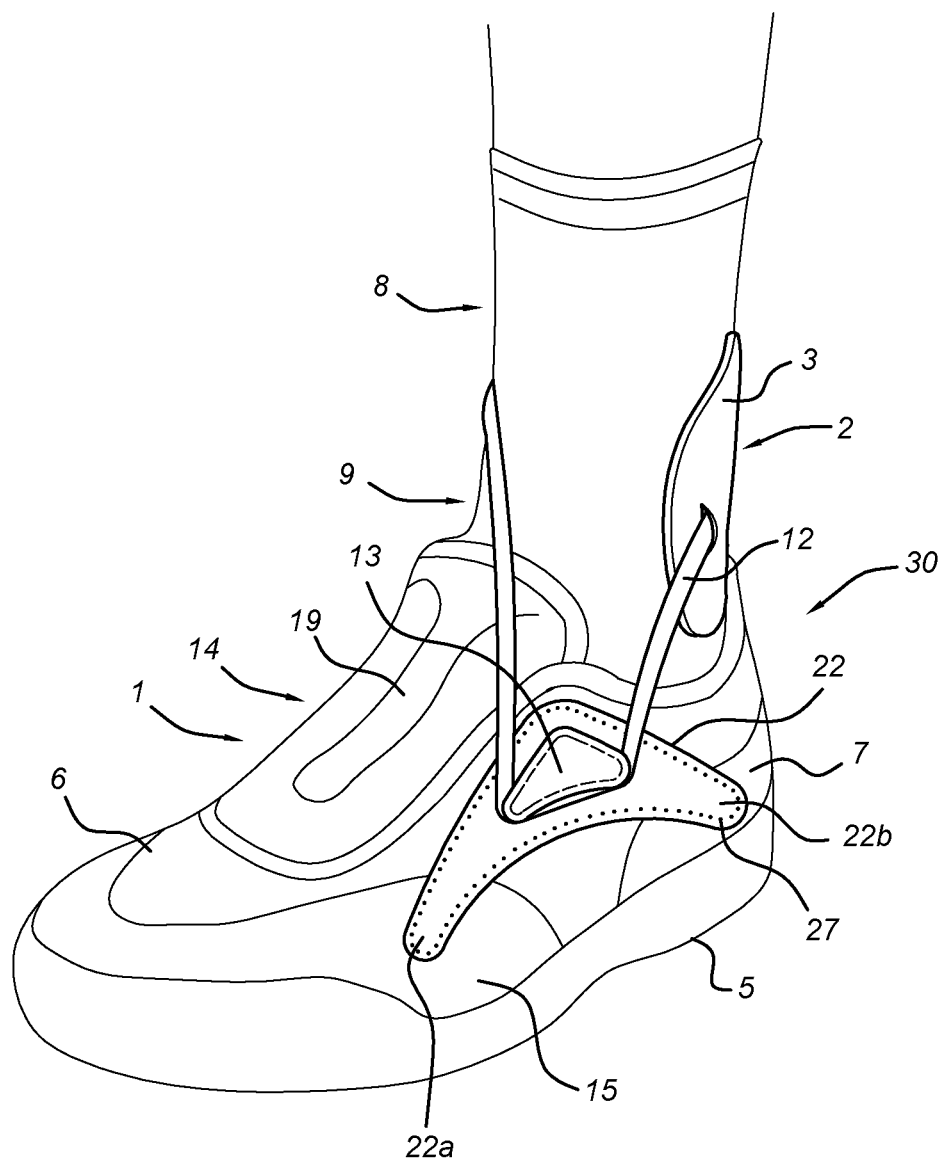

FIG. 5 shows the patch 22 in the shape of a capital lambda (Λ) which is attached to a shoe. The patch 22 has a first leg 22a which extends from the fixing means 13 in the direction of the sole 5 near the upper 6, and a second leg 22b which extends from the fixing means 13 in the direction of the sole 5 near the heel 7. The first and second legs 22a, 22b extend over part of the outside 15 of the shoe but do not touch the sole 5. The patch 22 is attached to the outside of the shoe with stitching but can also be attached by an adhesive. It is also possible to integrate the patch in the shoe. The patch can also be attached to or integrated into the inside 14 of the shoe depending on the desired reinforcement of the ankle.

LIST OF REFERENCE NUMERALS

1 Shoe
2 Device
3 Clip
4 -
5 Sole
6 Upper
7 Heel
8 Lower leg
9 Ankle
10 First end
11 Second end
12 Connecting means
13 Fixing means
14 Inside of shoe
15 Outside of shoe
16 Second fixing means
17 Lateral malleolus
18 Medial malleolus
19 Instep part of shoe
19' Foot instep
20 Fixing ring
21 Strap
21a Outer part of strap
21b Instep part of strap
21' Strap
21'a Upper part of strap
21'b Heel part of strap
22 Fixing element/patch
22a Instep part of patch
22b Outside part of patch
23 Cavity for Achilles' tendon
24 Support part of lateral malleolus
25 Support part of medial malleolus
26 Outside of foot
27 Fixing means
28
29
30 Assembly according to the invention

The invention claimed is:

1. An assembly comprising a shoe fitted with an upper and a sole, and a device connected with the shoe, wherein the device comprises a shaped piece of a rigid material, the shaped piece comprising a first support part, a second support part and a rear region between said first and second support parts, wherein the first and second support parts are wider than the rear region,
wherein the assembly comprises a connecting means comprising a first and a second connecting part,
wherein the first part extends at an angle of less than 90° in relation to the sole between the first support part of the shaped piece and a fixing means connected with the shoe, and the second part extends at an angle of less than 90° in relation to the sole between the second support part of the shaped piece and the fixing means, and wherein the shaped piece has an inflection between the rear region and each of the first and second support parts so that an outwardly concave region is formed between the rear region and each of the first and second support parts, and wherein the concave regions delimit a cavity region, and wherein the cavity region is outwardly convex.

2. The assembly according to claim 1, wherein the first and second support parts define an opening.

3. The assembly according to claim 1, wherein the connecting means is attached to at least one of an inside and outside of the upper.

4. The assembly according to claim 1, wherein the connecting means comprises a first and a second end wherein the first end is attached to the shaped piece and the second end is attached to the upper.

5. The assembly according to claim 1, wherein the fixing means is attached to the shoe at a transition between an instep and a side of the shoe, wherein the fixing means is located between the connecting means and the upper.

6. The assembly according to claim 1, wherein the connecting means comprises a further connecting part with a first and a second part, wherein the first part extends between the sole of the shoe near the upper and the fixing means, and the second part extends between the fixing means and the sole of the shoe near the heel.

7. The assembly according to claim 1, wherein the connecting means comprises a fixing element with a first and a second part, wherein the first part extends from the fixing means in the direction of the sole of the shoe near the upper, and the second part extends from the fixing means in the direction of the sol of the shoe near the heel.

8. The assembly according to claim 7, wherein the fixing element comprises a patch, wherein the first and the second part of the patch comprise fixing means for attachment to the shoe.

9. The assembly according to claim 1, wherein the fixing means comprises an engaging means for engaging the connecting means.

10. The assembly according to claim 9, wherein the engaging means and fixing means form an integral unit.

11. A shaped piece suitable for use in an assembly comprising a shoe and a device connected with the shoe to support the ankle, wherein the shaped piece comprises region,
   a first support part and a second support part and a rear region arranged between the first and second support parts,
   wherein the first and second support parts are wider than the rear region, and
   wherein the shaped piece (3) is formed of a rigid material, and the shaped piece has an inflection between the rear region and each of the first and second support parts so that an outwardly concave region is formed between the rear region and each of the first and second support parts, and wherein the concave regions delimit a cavity region, and wherein the cavity region is outwardly convex.

12. The shaped piece according to claim 11, wherein the first and second support parts define an opening.

13. The shaped piece according to claim 11, wherein reinforcements are located to the rear region.

14. A shoe configured for use in an assembly comprising a shoe and a device connected with the shoe to support the ankle,
   wherein the device comprises a shaped piece of rigid material, the shaped piece comprising a rear region between a first support part and a second support part,
   wherein the first and second support parts are wider than the rear region, and wherein the shaped piece has an inflection between the rear region and each of the first and second support parts so that an outwardly concave region is formed between the rear region and each of the first and second support parts, and wherein the concave regions delimit a cavity region, and wherein the cavity region is outwardly convex
   wherein the assembly comprises a connecting means,
   wherein the connecting means comprises comprise a first and a second connecting part,
   wherein the first part extends at an angle of less than 90° in relation to the sole between the first support part of the shaped piece and a fixing means connected with the shoe, and the second part extends at an angle of less than 90° in relation to the sole between the second support part of the shaped piece and the fixing means
   wherein the shoe is fitted with an upper and a sole and is provided with a fixing means for attaching a connecting means to the upper.

15. The shoe according to claim 14, wherein the fixing means is attached to an outside of the upper.

16. The shoe according to claim 14, wherein the fixing means is attached to the shoe at a transition between an instep and a side of the shoe, wherein the fixing means is located between the connecting means and the upper.

17. The shoe according to claim 14, wherein the fixing means comprises a fixing ring.

18. A set comprising a shaped piece and a fixing means,
   wherein the shaped piece comprises a first support part and a second support part and a rear region between said first and second support parts,
   wherein the first and second support parts are wider than the rear region, and
   wherein the shaped piece is formed of a rigid material,
   wherein the shaped piece has an inflection between the rear region and each of the first and second support parts so that an outwardly concave region is formed between the rear region and each of the first and second support parts, and wherein the concave regions delimit a cavity region, and wherein the cavity region is outwardly convex,
   and wherein the fixing means attachable to a shoe, the fixing means comprising a patch having a first and a second part, wherein the first part and the second part extend from each other at an angle between 0° and 180°.

19. The set according to claim 18, wherein the fixing means comprises an engaging means for engaging the connecting means.

20. The set according to claim 18, wherein the engaging means and the fixing means form an integral whole.

* * * * *